(12) United States Patent
Salamone et al.

(10) Patent No.: US 8,088,594 B2
(45) Date of Patent: Jan. 3, 2012

(54) RISPERIDONE IMMUNOASSAY

(75) Inventors: Salvatore J. Salamone, Stockton, NJ (US); Jodi Blake Courtney, Doylestown, PA (US); Daniel J. Cline, Allentown, PA (US); Howard Sard, Arlington, MA (US); Vishnumurthy Hegde, Chelmsford, MA (US)

(73) Assignee: Saladax Biomedical Inc., Bethlehem, PA (US)

( * ) Notice: Subject to any disclaimer, the term of this patent is extended or adjusted under 35 U.S.C. 154(b) by 0 days.

(21) Appl. No.: 12/724,780

(22) Filed: Mar. 16, 2010

(65) Prior Publication Data

US 2011/0229979 A1 Sep. 22, 2011

(51) Int. Cl.
*G01N 33/53* (2006.01)
*G01N 33/543* (2006.01)
*C07K 1/10* (2006.01)

(52) U.S. Cl. ....... 435/7.93; 435/7.1; 435/7.92; 436/501; 436/518; 436/523; 436/815; 530/388.9; 530/402; 530/403

(58) Field of Classification Search .................. None
See application file for complete search history.

(56) References Cited

U.S. PATENT DOCUMENTS

| 6,544,559 | B2 | 4/2003 | Mesens et al. | |
|---|---|---|---|---|
| 2006/0216769 | A1* | 9/2006 | Salamone et al. | 435/7.92 |
| 2007/0015290 | A1* | 1/2007 | Raj | 436/514 |
| 2008/0214808 | A1* | 9/2008 | Spittaels et al. | 544/282 |
| 2008/0287658 | A1 | 11/2008 | Salamone | |
| 2009/0306228 | A1 | 12/2009 | Mickle et al. | |

FOREIGN PATENT DOCUMENTS

WO 2009040409 A1 4/2009

OTHER PUBLICATIONS

The International Search Report and Written Opinion by the International Searching Authority, issued on Apr. 27, 2011, in the PCT application No. PCT/US11/25893.

* cited by examiner

*Primary Examiner* — Shafiqul Haq
*Assistant Examiner* — Galina Yakovleva

(57) ABSTRACT

Novel conjugates and immunogens derived from risperidone and antibodies generated by these immunogens are useful in immunoassays for the quantification and monitoring of risperidone and paliperidone in biological fluids.

20 Claims, No Drawings

RISPERIDONE IMMUNOASSAY

FIELD OF THE INVENTION

This invention relates to the field of immunoassays for determining the presence and/or quantifying the amount of risperidone and its pharmacologically active metabolite paliperidone in human biological fluids in order to rapidly determine optimal drug concentrations during treatment.

BACKGROUND OF THE INVENTION

Schizophrenia is a severe psychiatric disorder affecting approximately 1% of the world's population. Clinical symptoms of schizophrenia include delusions, auditory hallucinations, disorganized thoughts and speech, social withdrawal, lack of motivation, and cognitive dysfunction such as disorganized thinking and memory impairments. This disorder is believed to be caused by a combination of neurological defects including dopamine and serotonin levels, and inhibitory interneuron deficiencies (Freedman, 2003, New Eng. J. Med., 349(18): 1738-1749). Schizophrenia can be treated with drugs which target neurotransmitters and receptors, commonly referred to as anti-psychotic or neuroleptic drugs.

One class of anti-psychotic drug termed "atypical anti-psychotics" or "second generation anti-psychotics" includes the benzisoxazole derivative, risperidone (I). Risperidone, marketed under Risperdal® by Janssen-Cilag in the United States, targets the serotonin ($5\text{-}HT_{2A}$) and dopamine ($D_2$) receptors, blocking the uptake of their respective neurotransmitters (Package-Insert-Risperdal, 2009, Janssen Cilag). Risperidone is metabolized in humans by cytochrome P450 isoform CYP2D6 to the biologically active 9-hydroxy metabolite, paliperidone (II). Since both have been shown to have similar in vitro efficacy, together they constitute an "active moiety," and should be monitored collectively (Mannens et al., 1993, Drug Met. & Disp., 21(6): 1134-1141). Paliperidone itself has been approved by the FDA recently as a treatment for schizophrenia, marketed under Invega® by Janssen Pharmaceutica (Package-Insert-Invega, 2009, Janssen Pharmaceutica).

Risperidone has the following formula:

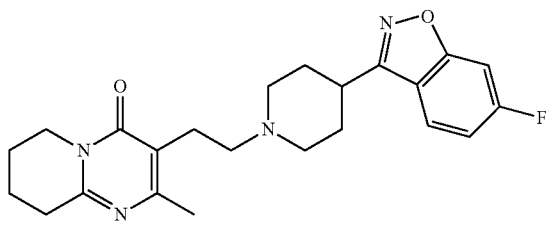

I

Paliperidone has the following formula:

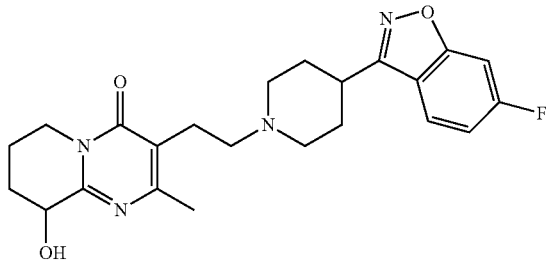

II

The "active moiety" of risperidone and paliperidone has been shown to have up to a 13-fold inter-patient variability in plasma steady-state concentrations and that this variability can impact efficacy and safety (Spina et al., 2001, Psychopharmacol., 153(2): 238-243; Aravagiri et al., 2003, Ther. Drug Monitor., 25(6): 657-664; Riedel et al., 2005, Eur. Arch. Psych. and Clin. Neurosci., 255(4): 261-268).

Since efficacy of risperidone and paliperidone is improved at higher trough levels and that the drug exhibits wide intra-patient pharmacokinetic variability monitoring concentrations of this drug in blood and adjusting to target levels would be of value in increasing efficacy and minimizing toxicity (Raggi et al., 2004, Med. Chem. Rev., 1: 299-316; Musenga et al., 2009, Curr. Med. Chem., 16(12): 1463-1481). The degree of intra- and inter-individual pharmacokinetic variability of risperidone and its derivative has been reported to be 13-fold and is impacted by many factors, including:

Age
Weight
Organ function
Drug-drug interaction
Genetic regulation
Compliance

As a result of this variability, equal doses of the same drug in different individuals can result in dramatically different clinical outcomes. The effectiveness of the same dosage of risperidone and paliperidone varies significantly based upon individual drug clearance and the ultimate serum drug concentration in the patient. Therapeutic drug management would provide the clinician with insight on patient variation in drug administration. With therapeutic drug management, drug dosages could be individualized to the patient, and the chances of effectively treating the disorder without the unwanted side effects would be much higher.

In addition, therapeutic drug management of risperidone and paliperidone would serve as an excellent tool to ensure compliance (Valenstein et al., 2006, J. Clin. Psych., 67(10): 1542-1550; Treur et al., 2009, BMC Health Serv. Res., 9: 9) in administering anti-psychotic drugs with the actual prescribed dosage and achievement of the effective serum concentration levels. Routine therapeutic drug management of risperidone and paliperidone would require the availability of simple automated tests adaptable to general laboratory equipment. The use of liquid chromatography (LC) with UV or mass spectroscometry detection to determine the concentration of risperidone and paliperidone in human blood and plasma has been described (Balant-Gorgia, et al., 1999, Ther. Drug Monitor., 21(1): 105-115; Schatz et al., 2000, Pharmacol., 60(1): 51-56; Frahnert et al., 2003, J. Chrom. B, 794(1): 35-47; Zhang et al., 2008, Biomed. Chrom., 22(7): 671-687). These methods are labor intensive, requiring liquid-liquid or solid phase extractions, use expensive equipment and are not amenable to routine clinical laboratory use. To date, there are no immunoassays for measuring risperidone and/or paliperidone in human biological fluids of patients treated with these anti-psychotic agents.

As seen from the foregoing, there are no immunoassays for determining the presence and/or quantifying the amount of risperidone and paliperidone in human biological fluids. Routine therapeutic drug management of risperidone and paliperidone by immunoassays would provide simple automated tests adapted to standard laboratory equipment. However, in order to provide such immunoassays, antibodies selective to risperidone and paliperidone must be produced. The derivatives and immunogen used in this assay must impart through these corresponding antibodies produced selective reactivity to risperidone and paliperidone without any substantial cross reactivity to other therapeutically active or inactive, or pharmacologically active or inactive metabolites of risperidone and paliperidone. In order to be effective in monitoring drug levels, the antibodies should be selective to risperidone and paliperidone and not cross reactive with pharmaceutically or pharmacologically inactive metabolites of risperidone and paliperidone. The principle pharmaceutically or pharmacologically inactive metabolites are 7-hydroxy-risperidone (V) or N-dealkyl-risperidone (VI) (Mannens, et al., 1993, Drug Met. & Disp., 21(6): 1134-1141; He et al., 1995, Int. Clin. Psychopharmacol., 10(1): 19-30), which metabolites have the formulae:

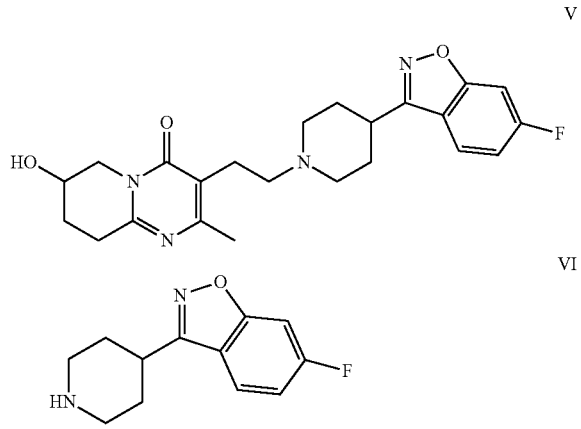

In order to be effective in an immunoassay, these antibodies should have substantially low reactivity to the pharmaceutically or pharmacologically inactive metabolite, 7-hydroxy-risperidone V, while having substantially no or any reactivity to the other pharmaceutically or pharmacologically inactive metabolites, particularly N-dealkyl-risperidone VI. This is so since the metabolite, 7-hydroxy-risperidone V is only produced from risperidone and paliperidone in very small amounts.

SUMMARY OF INVENTION

In accordance with this invention, a new class of antibodies have been produced which are substantially selectively reactive to risperidone and paliperidone so as to be selectively reactive with risperidone and paliperidone with little substantial reactivity to their pharmacologically or pharmaceutically inactive metabolite, 7-hydroxy-risperidone and without any substantial cross reactivity to their other pharmacologically or pharmaceutically inactive metabolites such as N-dealkyl-risperidone. By selectively reactivity, it is meant that this antibody reacts with the risperidone and paliperidone and has little substantial reactivity with the pharmacologically inactive risperidone and paliperidone metabolite, 7-hydroxy-risperidone and does not have substantial cross-reactivity with the other pharmacologically inactive risperidone and paliperidone metabolites, particularly N-dealkyl-risperidone. These properties are important for providing the immunoassay of this invention since the metabolite, 7-hydroxy-risperidone V, is only produced from risperidone and paliperidone in very small amounts, less than 5% by weight, based on the weight of the risperidone and paliperidone used in forming this metabolite (Mannens, et al., 1993, Drug Met. & Disp., 21(6): 1134-1141). Therefore, in carrying out these immunoassays, on a human fluid sample, there will be little, if any, 7-hydroxy-risperidone in the human sample of the patient treated with risperidone and paliperidone. With this reactivity and cross reactivity of these antibodies to these non-pharmaceutically or pharmacologically active metabolites of risperidone and paliperidone, these metabolites do not interfere with an accurate determination, by an immunoassay, of the presence and the amount of risperidone and paliperidone in human biological fluids.

It has been found that by using immunogens which are conjugates of an immunogenic polyamine polymer with a compound of the formula:

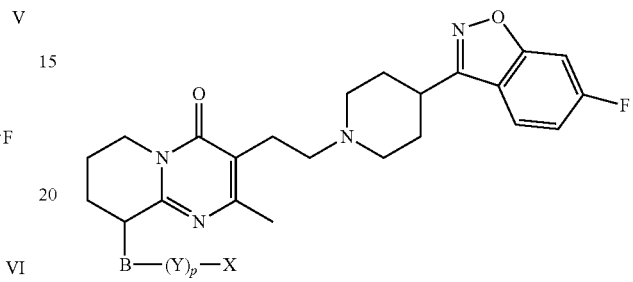

wherein B is;

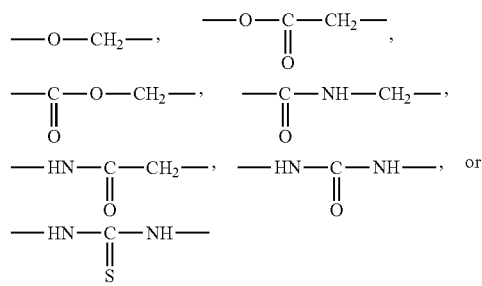

Y is an organic spacing group;
X is a terminal functional group capable of binding to a carrier; and
p is an integer from 0 to 1;

antibodies are produced which are selective for risperidone and paliperidone in that they have substantially little reactivity with the pharmacologically inactive risperidone and paliperidone metabolite, 7-hydroxy-risperidone and do not substantially cross-react with the other pharmacologically inactive risperidone and paliperidone metabolites, particularly N-dealkyl-risperidone.

The provision of these antibodies which substantially selectively react with risperidone and paliperidone and which have little or no cross reactivity with pharmacologically inactive risperidone and paliperidone metabolites, as described above, allows one to produce an immunoassay which can specifically detect and quantify so as to monitor risperidone and paliperidone in the fluid samples of patients being treated with risperidone and paliperidone. Also included within this invention are reagents and kits for said immunoassay.

DETAILED DESCRIPTION

In accordance with this invention, a new class of antibodies is provided which substantially selectively reacts with risperidone and paliperidone and do not or have little substantial reactivity or cross reactivity with the metabolites as mentioned hereinabove. It has been discovered that through the use of these derivatives of risperidone of formula III as immunogens, this new class of antibodies of this invention is provided. It is through the use of these antibodies that an immunoassay, including reagents and kits for such immunoassay for detecting and/or quantifying risperidone and paliperidone in blood, plasma or other body fluid samples has been developed. By use of this immunoassay, the presence and amount of risperidone and paliperidone in body fluid samples of patients being treated these therapeutic agents can be detected and/or quantified. In this manner, a patient being treated with risperidone or paliperidone can be monitored during therapy and his treatment adjusted in accordance with said monitoring. By means of this invention one achieves the therapeutic drug management of risperidone and/or paliperidone in psychotic patients, particularly schizophrenic patients, being treated with risperidone or paliperidone as therapeutic anti-psychotic agents. The therapeutic anti-psychotic agents to be detected are risperidone of formula I and/or its pharmacologically active metabolite which is paliperidone of formula II.

The antibodies of this invention provide a means for detecting the active pharmaceutically anti-psychotic drugs risperidone and paliperidone. Since the antibodies of this invention are reactive with both risperidone and paliperidone it can be utilized detecting both risperidone and paliperidone. Therefore one can either use them in an immunoassay for patients treated with risperidone and as well as in an immunoassay for patients treated with paliperidone so as to monitor the administration of either one of these anti-psychotic drugs. This is true since paliperidone is the pharmaceutically active metabolite of risperidone. In this way, patients treated with risperidone can be monitored to determine the presence of either risperidone or paliperidone or both in the patient's sample. The quantification of the amount of both of these drugs in the patient's sample where the patient is treated with risperidone will determine how much risperidone should be administered to the patient and how to control risperidone therapy. With respect to paliperidone, since it is a metabolite of risperidone, there will be little, if any, risperidone in the human sample of the patient treated with paliperidone. Hence by this immunoassay, patients treated with paliperidone can be monitored to determine the presence of paliperidone in the patient's sample. In the same way, the quantification of the amount of paliperidone in the patient's sample where the patient is treated with paliperidone will determine how much paliperidone should be administered to the patient and how to control paliperidone therapy.

The immunoassay of this invention is carried out by providing a mixture containing the sample of the patient treated with one or both of these anti-psychotic drugs and providing a mixture containing this sample with the antibody of this invention and the conjugate of a carrier of the ligand of formula III. In this manner, pharmaceutically active anti-psychotic drug and the conjugate in said sample will bind with the antibody and from this binding, and from determining the amount of conjugate, one can calculate the amount of the anti-psychotic drugs in the patient's sample.

Any patient's sample can be used. Generally it is preferred that the patient sample can be a blood sample taken from the patient being treated with either one or both of these drugs. This will provide an easy way to continuously monitor the treatment of the patient with these anti-psychotic drugs.

The reagents utilized in the assay of this invention are conjugates of a polymeric carrier with the compounds of formula III. These conjugates are competitive binding partners with the risperidone and paliperidone present in the sample for the binding with the antibodies of this invention. Therefore, the amount of conjugate reagent which binds to the antibody will be inversely proportional to the amount of risperidone and paliperidone in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of risperidone and paliperidone in a sample is determined by correlating the measured amount of the bound or unbound conjugate produced by the risperidone and paliperidone in the sample with values of the bound or unbound conjugate determined from standard or calibration curve obtained with samples containing known amounts of risperidone and/or paliperidone, which known amounts are in the range expected for the sample to be tested. These studies for producing calibration curves are determined using the same immunoassay procedure as used for the sample.

DEFINITIONS

Throughout this description the following definitions are to be understood:

The term "Ph" as used throughout this application designates a phenyl radical. The term "alkylene" designates a divalent saturated straight or branch chain hydrocarbon substituent containing from one to ten carbon atoms.

The terms "immunogen" and "immunogenic" refer to substances capable of eliciting, producing, or generating an immune response in an organism.

The term "conjugate" refers to any substance formed from the joining together of separate parts. Representative conjugates in accordance with the present invention include those formed by the joining together of a small molecule, such as the compound of formula III, and a large molecule, such as a carrier or a polyamine polymer, particularly protein. In the conjugate the small molecule maybe joined at one or more active sites on the large molecule. The term conjugate includes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is risperidone.

As used herein, a "spacing group" or "spacer" refers to a portion of a chemical structure which connects two or more substructures such as haptens, carriers, immunogens, labels, or tracers through a functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing to groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join at one or more positions with a hapten, in this case risperidone, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly(amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains poly(amino acid) residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (µm) and not more than about 100 µm, and usually about 0.05 µm to 10 µm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with, or otherwise attached to a polyamine polymer to provide one or more reactive sites for bonding to the terminal functional group X in the compounds of the formula III.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for risperidone and paliperidone. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In an immunoassay based upon an antibody, a conjugate of risperidone is constructed to compete with the risperidone and paliperidone in the sample for binding sites on the antibody. In the immunoassay of this invention, the reagents of formula III are the oxygen substituted risperidone derivatives formed on the 9-hydroxyl group of paliperidone of formula II. In the compounds of formula III the linker spacer constitutes the "Y—X" portion of this molecule. These linker X and the spacer Y are conventional in preparing conjugates for immunoassays and immunogens for producing antibodies. Any of the conventional spacer-linking groups utilized to prepare conjugates for immunoassays and immunogens for producing antibodies can be utilized in the compounds of formula III. Such conventional linkers and spacers are disclosed in U.S. Pat. No. 5,501,987 and U.S. Pat. No. 5,101,015.

The conjugates as well as the immunogens, are prepared from the compound of the formula II. In the conjugates or immunogens of the carrier with the hapten, the carriers are linked in one or positions to one or more reactive amino groups contained by the polyamine polymer portion of the carrier to the hapten which has the formula:

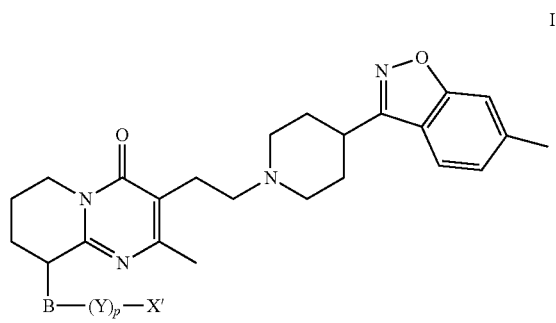

IV wherein X' is —CH$_2$ or a functional linking group and B, p and Y are as above;

Among the preferred spacer groups are included the spacer groups hereinbefore mentioned. Particularly preferred spacing groups are groups such as alkylene containing from 1 to 10 carbon atoms,

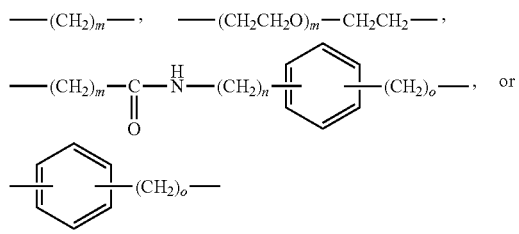

wherein n and o are integers from o to 6, and m is an integer from 1 to 10 with alkylene being the especially preferred spacing group.

In the compounds of formula IV, where X' is a functional group linking the spacer, preferably through a reactive amine group on the polymeric carrier. The group X' is the result of the terminal functional group X in the compounds of formula III binding to the reactive amino group in the polyamine polymer of the carrier or the immunogen. Any terminal functional group capable of reacting with an amino group can be utilized as the functional group X in the compounds of formulae III. These terminal functional groups preferably included within X are:

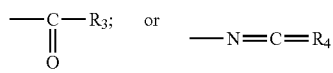

wherein R$_3$ is hydrogen, halogen, hydroxyl, or taken together with an attached oxygen atom forms a reactive ester, and R$_4$ is oxygen or sulfur. The radical —N═C═R$_4$ can be an isocyanate or an isothiocyanate. The active esters formed by R$_3$ include imidoester, such as N-hydroxysuccinamide, 1-hydroxy benzotriazole and p-nitrophenyl ester. However any active ester which can react with an amine group can be used.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing hapten of formula III and the reactive amino groups on the polyamine polymer contained by the carrier or immunogen can be established using a variety of methods known to one skilled in the art. It is frequently preferable to form amide bonds. Amide bonds are formed by first activating the carboxylic acid moiety which forms X in the compounds of formula III and then reacting this carboxy group with a leaving group reagent (e.g., N-hydroxysuccinimide, 1-hydroxybenzotriazole, p-nitrophenol and the like). Any activating reagent such as dicyclohexylcarbodiimide, diisopropylcarbodiimide and the like can be used. The carboxylic acid moiety which forms X in the compounds of formula III can also be activated by conversion to the respective acid halides using thionyl chloride, thionyl bromide, and the like. The activated form of the carboxyl group in the risperidone hapten of formula III is then reacted with a buffered solution containing the carrier with the reactive amino group.

Where X, in the compounds of formula III contains an aldehyde radical, these compounds may be connected to the free amino group of the polyamine polypeptide on the carrier through an amine linkage by reductive amination. Any conventional method of condensing an aldehyde with an amine such as through reductive amination can be used to form this linkage. In this case, X' in the ligand portions of formula IV is —CH$_2$—.

On the other hand where X is a terminal isocyanate or thioisocyanate radical —N═C═R$_4$, in the compound of formula III, these radicals when reacted with the free amine of a polyamine polymer to produce the conjugate or immunogen of formula IV where X' is with the amino group on the polyamine carrier or the immunogenic polypeptide.

The compound of formula III can be converted into the immunogens and/or the conjugate reagents of this invention by reacting these compounds with a carrier containing a polyamine or a polypeptide. The same polypeptide can be utilized as the carrier and as the immunogenic polymer in the immunogen of this invention provided that polyamine or polypeptide is immunologically active. However, to form the conjugates, these polymers need not produce an immunological response as is needed for the immunogens. In accordance with this invention, the various functional group represented by X in the compounds of formula III can be conjugated to the carrier containing polymer with a reactive amino group by conventional means of attaching a functional group to an amino group contained within the polymer. In accordance with a preferred embodiment, in the compound of formula III, X is a carboxylic acid group or an active ester thereof.

The compound of formula III can be formed from a compound of the formula:

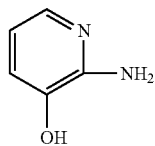

IX-A

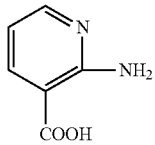

IX-B

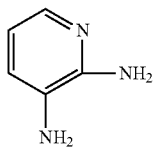

IX-C

The compounds of the formula III are formed from compounds of the formula

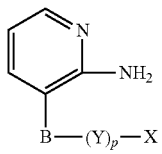

X

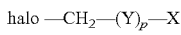

Where B, Y and X are as above.

In converting the compound of formula IX-A to derivatives of the compound of formula X where B is —O—CH$_2$—, the compound of formula IX-A is reacted with a compound of the formula halo —CH$_2$—(Y)$_p$—X     XI-A wherein p, Y and X are as above.

In forming these derivatives, any conventional means of reacting an alcohol to form an ether can be utilized in condensing the halo compound of formula XI-A with the hydroxy group on the compound of formula IX-A. The use of a halide in the compound of formula XI-A provides an efficient means for forming an ether by condensing with the alcohol. On the other hand, were the compound of formula XI-A to contain functional groups which may interfere with this reaction to form these derivatives, these functional groups can be protected by means of suitable protecting groups which can be removed after this reaction as described hereinabove.

In the compound of formula X where B is

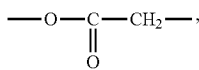

the free hydroxy group in the compound of formula IX-A is reacted with a compound of formula

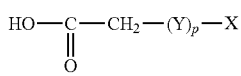

XI-B wherein Y, X, and p are as above
utilizing any conventional means of esterification. Prior to esterification, the amino group on the compound of formula IX-A can be protected by utilizing any conventional amino protecting group.

The derivatives of the compound of formula X where B is,

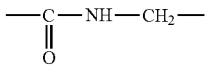

are produced by reacting the carboxyl group on the compound of formula IX-B with an amino compound of the formula:

NH$_2$—CH$_2$—(Y)$_p$—X     XI-C wherein X, Y and p are as above
after first activating the carboxyl group on the compound of formula IX-C using any conventional means of carboxylate activation mentioned hereinabove. Prior to this reaction, the reactive group on the compound of formula XI-C may be protected as described hereinabove with a conventional protecting group. These protecting groups can be removed after this amidation by conventional means such as described hereinbefore. Any means of protecting an amino group can be used of the compound of formula X. The amino protecting group can be removed by conventional means.

The derivatives of the compound of formula X where B is

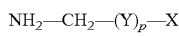

are produced by reacting the carboxyl group on the compound of formula IX-B with an hydroxy compound of the formula:

HO—CH$_2$—(Y)$_p$—X XI-D wherein X, Y and p are as above
after first activating the carboxyl group on the compound of formula IX-B using any conventional means of carboxylate activation mentioned hereinabove. Prior to this reaction, the reactive group on the compound of formula XI-D may be protected as described hereinabove with a conventional protecting group. These protecting groups can be removed after this esterification by conventional means such as described hereinbefore. Any means of protecting an amino group can be used of the compound of formula X. The amino protecting group can be removed by conventional means.

The derivatives of the compound of formula X where B is

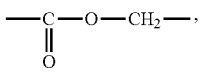

are produced by reacting the amine group on the compound of formula IX-C with a carboxylate containing compound of the formula:

HOOC—CH$_2$—(Y)$_p$—X     XI-E wherein X, Y and p are as above
The ortho-positioned amine on the compound of formula IX-C must be selectively protected as described hereinabove with a conventional protecting group prior to reaction. The amidation reaction proceeds after activation of the carboxylate of formula XI-E using any conventional means of carboxylate activation mentioned hereinabove. Prior to this reaction, the reactive group on the compound of formula XI-E may be protected as described hereinabove with a conventional protecting group. These protecting groups can be removed after this amidation by conventional means such as described hereinbefore.

The derivatives of the compound of formula X where B is

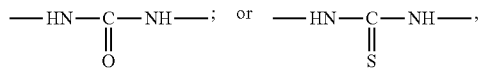

are produced by reacting the amine group on the compound of formula IX-C with a isocyante or isothiocyante containing compound of the formula:

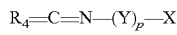      XI-F wherein X, Y and p are as above, and $R_4$ is O or S

The ortho-positioned amine on the compound of formula IX-C must be selectively protected as described hereinabove with a conventional protecting group prior to reaction. The condensation reaction proceeds after addition of formula XI-F to a buffered solution of compound IX-C. Prior to this reaction, the reactive group on the compound of formula XI-F may be protected as described hereinabove with a conventional protecting group. These protecting groups can be removed after this condensation by conventional means such as described hereinbefore.

The compound of formula X can be converted to the compound of formula III utilizing any of the methods of synthesizing paliperidone from the compound of formula IX. In this procedure the functional group X in the compound of formula X is protected by a suitable protecting group and after the formation of the compound of formula III, the protecting group can be removed by conventional means.

Antibodies

The present invention also relates to novel antibodies including monoclonal antibodies to risperidone and paliperidone produced by utilizing the aforementioned immunogens. In accordance with this invention it has been found that these antibodies produced in accordance with this invention are selectively reactive with risperidone and paliperidone. By being selectively reactive, it is meant that this antibody reacts with the risperidone and paliperidone and has little substantial reactivity with the pharmacologically inactive risperidone and paliperidone metabolite, 7-hydroxy-risperidone which reactivity is less than 40%, preferably less than 25%, based on its reactivity with both risperidone and paliperidone and does not substantially cross-react with the other pharmacologically inactive risperidone and paliperidone metabolites, particularly N-dealkyl-risperidone, which substantial non cross-reactivity to the other metabolites is less than 5% based on its reactivity with both risperidone and paliperidone. It is these selective reactive properties which provide an antibody for performing an immunoassay for accurately detecting the presence and/or quantifying the amount of risperidone and paliperidone in patient fluid samples.

The present invention relates to novel antibodies and monoclonal antibodies to risperidone and paliperidone. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and two or more subsequent booster shots of between 50 and 100 ug immunogen/mouse over a six month period. Through periodic bleeding, the blood samples of the immunized mice were observed to develop an immune response against risperidone and paliperidone binding utilizing conventional immunoassays. These methods provide a convenient way to screen for hosts which are producing antisera having the desired activity. The antibodies were also screened against the major metabolite of risperidone, paliperidone, and showed substantial binding to this compound.

The antibodies which are selectively reactive with the risperidone and paliperidone and have little substantial reactivity with the pharmacologically inactive risperidone and paliperidone metabolite, 7-hydroxy-risperidone, reactivity of less than 40%, preferably less than 25%, based on its reactivity with both risperidone and paliperidone and do not substantially cross-react with the other pharmacologically inactive risperidone and paliperidone metabolites, particularly, N-dealkyl-risperidone, substantial non-cross-reactivity to the other metabolites is less than 5%, based on its reactivity with both risperidone and paliperidone, can be produced utilizing the immunogen of formula III and by the screening method disclosed below. This screening method can be used to obtain antibodies which are reactive with both the risperidone and paliperidone chemotherapeutic agents, which are specific and selective to these chemotherapeutic agents having any desired relative reactivity with regard to these chemotherapeutic agents.

In preparing these antibodies, an immunogenic carrier can be conjugated with the immunogen of formula III and used to immunize host animals include rodents, such as, for example, mice, rats, rabbits, guinea pigs and the like, or higher mammals such as goats, sheep, horses and the like. Development of the immune response to the compound of formula III can be monitored by ELISA utilizing microtiter plates coated with a conjugate of BSA and the compound of formula III. Once the immune response has been sufficiently developed the spleen cells of the host animal can be isolated and fused with an immortalized cell line. With respect to producing monoclonal antibodies, the fused cells can be plated on 96-well plates and grown in the presence of a selective medium to select hybridoma cells. Hybridoma supernatants and antisera can be assayed for the presence of anti-risperidone antibodies by ELISA. Antibodies from wells that gave positive ELISA results can be tested for risperidone and paliperidone binding by indirect competitive microtiter plate assay. The $IC_{50}$ values of an analyte such as risperidone, paliperidone, and their metabolites, can be calculated from this assay. The $IC_{50}$ (inhibitory concentration at 50%) of an analyte in an assay is the concentration of that analyte in a sample at which the signal in the assay is 50% of the total signal for the assay in the absence of analyte in an inhibition assay. Selective reactivity of an analyte is calculated from a ratio of the $IC_{50}$'s expressed as a %: $100\%-([IC_{50}\text{-analyte}/(IC_{50}\text{-risperidone}+IC_{50}\text{-paliperidone})]\times 100)$. The calculation of the $IC_{50}$ is carried out according to the procedure found in The Immunoassay Handbook, pp 108-110, $3^{rd}$ edition, edited by D. Wild, published by Elsevier, Amsterdam, 2005. As seen from the formula, the $IC_{50}$ of an analyte is inversely proportional to the reactivity of the analyte. Cells from wells that gave 100% or approaching 100% can be subcloned by limiting dilution to isolate individual clones producing monoclonal anti-risperidone antibodies. Cells from wells that have desired relative reactivity with regard to risperidone and paliperidone can be subcloned by limiting dilution to isolate individual clones producing monoclonal anti-risperidone antibodies, sufficiently cross-reactive with paliperidone to also be selective for that drug.

Monoclonal antibodies are produced conveniently by immunizing Balb/c mice according to the above schedule followed by injecting the mice with 100 ug immunogen i.p. or i.v. on three successive days starting three or four days prior to the cell fusion. Other protocols well known in the antibody art may of course be utilized as well. The complete immunization protocol detailed herein provided an optimum protocol for serum antibody response for the antibody to risperidone or its pharmacologically active metabolite paliperidone.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In, the preferred embodiment of the invention the immortal cell may be a lymphoblastoid cell or a plasmacytoma cell such as a myeloma cell, itself an antibody producing cell but also malignant. Murine hybridomas which produce monoclonal antibodies to risperidone or its pharmacologically active metabolite paliperidone are formed by the fusion of mouse myeloma cells and spleen cells from mice immunized against risperidone-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutagenesis to produce Fab fragments or (Fab')$_2$ fragments. Single chain antibodies may be produced by joining VL and VH regions with a DNA linker (see Huston et al., 1988, *Proc. Natl. Acad. Sci. U.S.A.*, 85:5879-5883 and Bird et al., 1988, *Science*, 242:423-426)

The antibodies of this invention are substantially selectively reactive to risperidone and paliperidone with little substantial reactivity with their pharmacologically or pharmaceutically inactive metabolite, 7-hydroxy-risperidone, and without any substantial cross reactivity to their other pharmacologically or pharmaceutically inactive metabolites such as N-dealkyl-risperidone. By having little substantial reactivity with their pharmacologically or pharmaceutically inactive metabolite, 7-hydroxy-risperidone, it is meant that the antibodies of this invention have a reactivity to 7-hydroxy-risperidone, of less than 40%, preferably less than 25%, relative to their combined reactivity to both risperidone and paliperidone. By having no or being without any substantial cross-reactivity to the pharmacologically or pharmaceutically inactive metabolites other than 7-hydroxy-risperidone, it is meant that the antibodies of this invention have a cross reactivity relative to their combined reactivity to both risperidone and paliperidone to these other pharmacologically or pharmaceutically inactive metabolites such as N-dealkyl-risperidone, of less than 5%, preferably less than 2%.

Immunoassays

In accordance with this invention, the conjugates and the antibodies generated from the immunogens of these compounds of formula III can be utilized as reagents for the determination of risperidone and paliperidone in patient samples. This determination is performed by means of an immunoassay. Any immunoassay in which the reagent conjugates formed from the compounds of formula III compete with the risperidone and paliperidone in the sample for binding sites on the antibodies generated in accordance with this invention can be utilized to determine the presence of risperidone and paliperidone in a patient sample. The manner for conducting such an assay for risperidone and paliperidone in a sample suspected of containing risperidone and paliperidone, comprises combining an (a) aqueous medium sample, (b) an antibody to risperidone and paliperidone generated in accordance with this invention and (c) the conjugates formed from the compounds of formula III or mixtures thereof. The amount of risperidone and paliperidone in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of risperidone. In determining the amount of risperidone and paliperidone in an unknown sample, the sample, the conjugates formed from the compounds of formula III and the antibody may be added in any order.

Various means can be utilized to measure the amount of conjugate formed from the compounds of formula III bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. No. 4,269,511 and U.S. Pat. No. 4,420,568.

On the other hand, the antibody can be coated or absorbed on nanoparticles so that when these particles react with the risperidone conjugates formed from the compounds of formula V, these nanoparticles form an aggregate. However, when the antibody coated or absorbed nanoparticles react with the risperidone and paliperidone in the sample, the risperidone and paliperidone from the sample bound to these nanoparticles does not cause aggregation of the antibody nanoparticles. The amount of aggregation or agglutination can be measured in the assay mixture by absorbance.

On the other hand, these assays can be carried out by having either the antibody or the risperidone conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula III which is bound or unbound with the antibody. Other suitable labels include chromophores, fluorophores, etc.

As a matter of convenience, assay components of the present invention can be provided in a kit, a packaged combination with predetermined amounts of new reagents employed in assaying for risperidone and paliperidone. These reagents include the antibody of this invention, as well as, the conjugates formed from the compounds of formula V.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:
MsCl Methanesulfonyl chloride
DIPEA N—N'-Diisopropylethylamine
THF tetrahydrofuran
TFA trifluoroacetic acid
pTSA p-Toluenesulfonic acid
HATU O-(7-Azabenzotriazol-1-yl)-N,N,N',N'-tetramethyluronium hexafluorophosphate
DMF Dimethylformamide
DMSO Dimethylsulfoxide
s-NHS sulfo-N-hydroxy succinimide
EDC 1-(3-dimethylaminopropyl)-3-ethylcarbodiimide hydrochloride
KLH Keyhole Limpet Hemocyanin
BSA Bovine serum albumin
PBS Phosphate buffered saline
NaCl sodium chloride
HRP horse radish-peroxidase
ANS 8-Anilino-1-naphthalenesulfonic acid
TMB 3,3',5,5'-Tetramethylbenzidine
TRIS Tris(hydroxymethyl)aminomethane hydrochloride
di H2O deionized water The phosphate buffer composition has an aqueous solution containing
15.4 mM Sodium phosphate dibasic (Na$_2$HPO$_4$)
4.6 mM Sodium phosphate monobasic (NaH$_2$PO$_4$)
pH=7.2±0.10

In the examples, Schemes 1-2 below set forth the specific compounds prepared and referred to by numbers in the Examples. The schemes are as follows:

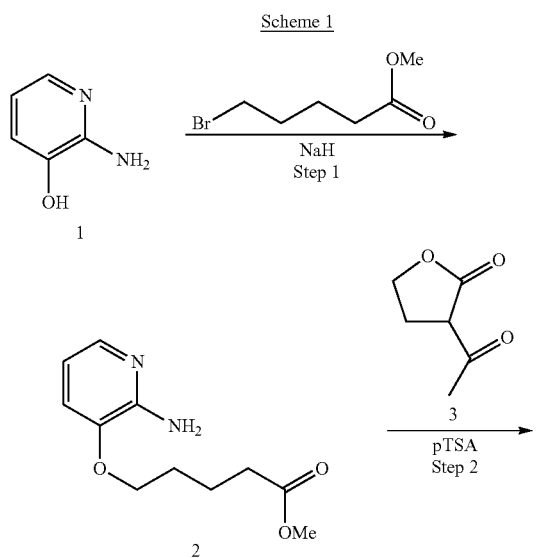

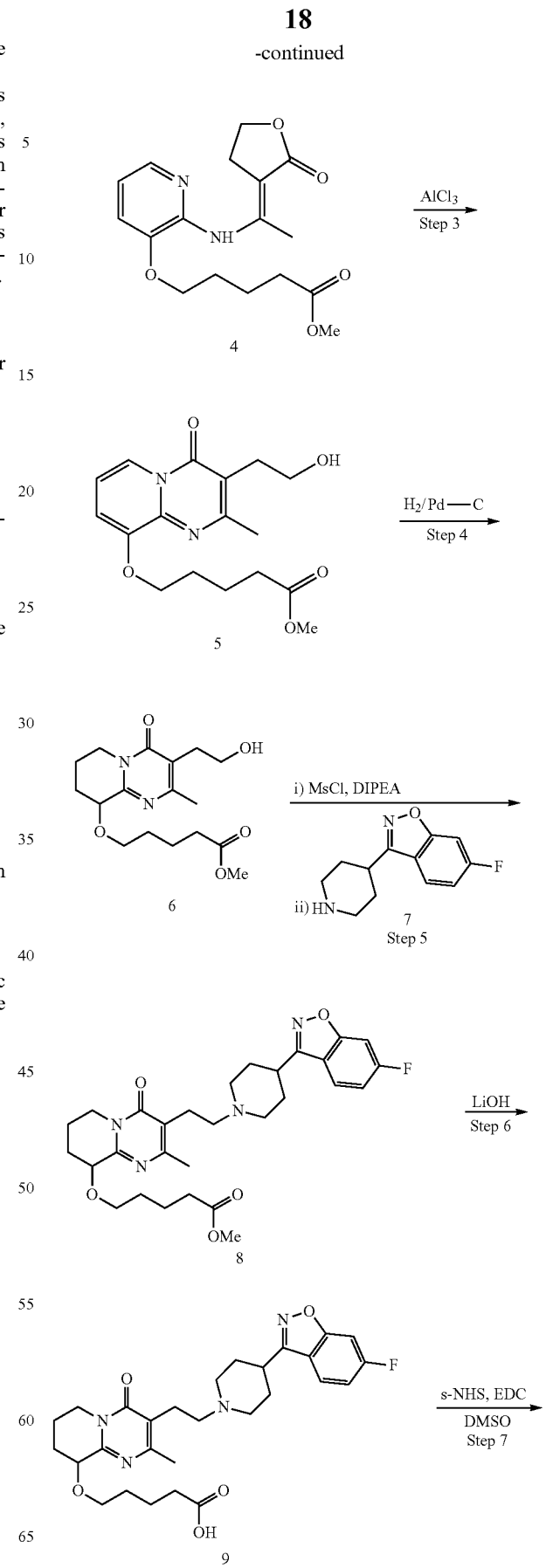

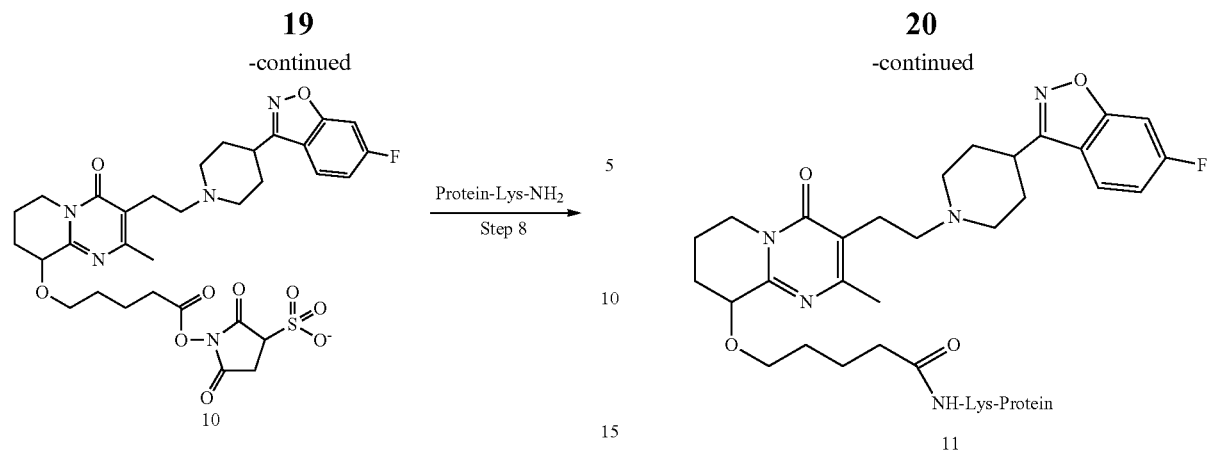
Scheme 2
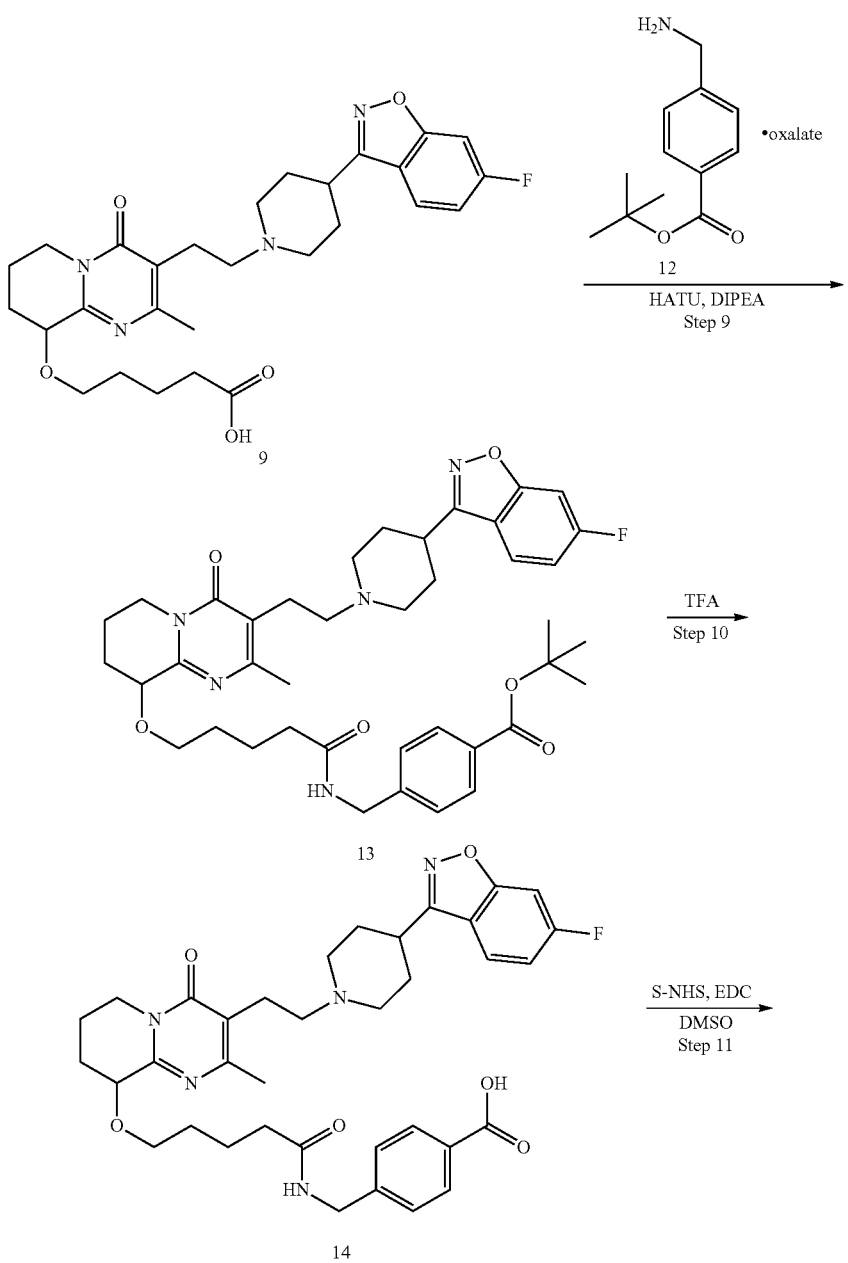

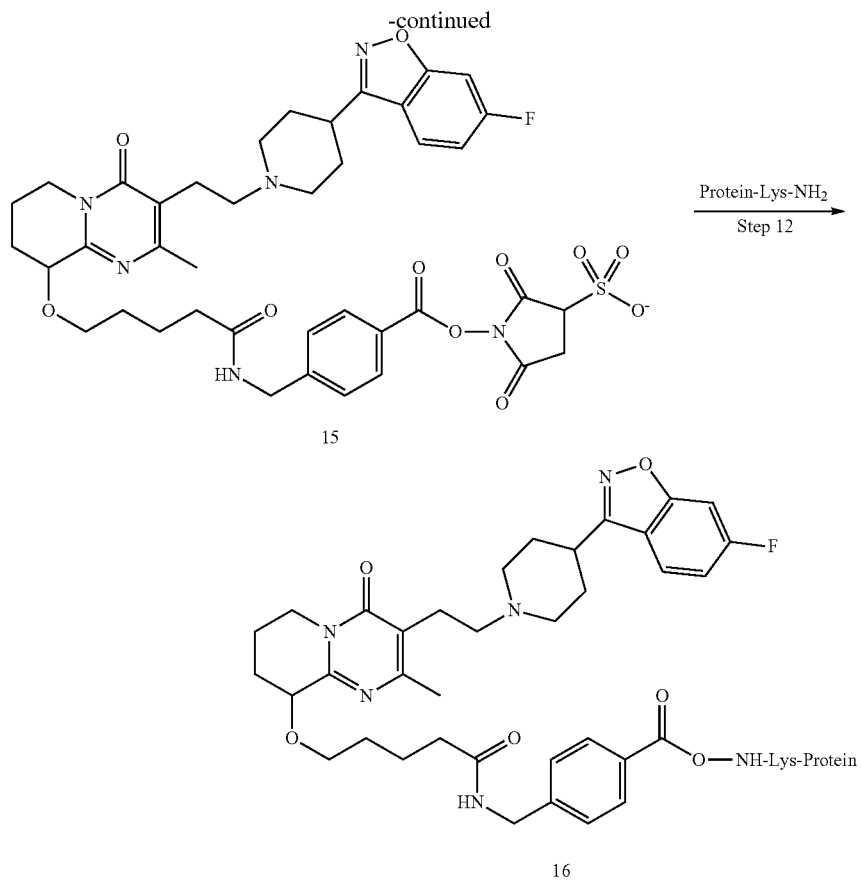

Example 1

Preparation of Risperidone (9-yloxy)pentanoic Acid Derivative [9] (Scheme 1)

Compound [1] (10.0 g, 90.8 mmol) was dissolved in anhydrous DMF (200 mL) at 0° C. under an N2 atmosphere. While stirring, NaH (60%, 3.62 g, 90.8 mmol) was added, and the mixture was allowed to warm to ambient temperature for 1 h. Methyl 5-bromopentanoate (17.72 g, 90.80 mmol) was then added to the reaction mixture and stirring was continued overnight. The reaction mixture was diluted with water, extracted with EtOAc. The extract was washed with water and then brine, dried (Na$_2$SO$_4$) and the solvent evaporated to isolate the crude product [2]. Impurities were removed by flash chromatography using 20-90% EtOAc/hexanes to isolate the pure compound [2] (12.80 g, 63%).

Compound [2] (12.80 g, 57.14 mmol), compound [3] (8.80 g, 68.57 mmol), and pTS.H$_2$O (2.0 g, 10.5 mmol) were dissolved in xylene (300 mL), and the resulting mixture was heated at reflux for 12 h under Dean-Stark conditions. After 12 h, xylene was removed under reduced pressure, sat. NaHCO$_3$ was added to the residue, and the slurry was extracted with EtOAc. The organic phase was washed with brine, dried (Na$_2$SO$_4$), and evaporated to isolate the crude product [4]. This material was triturated with a 1:1 mixture of ether/hexanes to isolate the pure compound [4] (10.40 g, 55%).

A mixture of compound [4] (9.90 g, 29.64 mmol) and AlCl$_3$ (1.98 g, 14.85 mmol) in anhydrous dichloroethane was heated at 95° C. under N$_2$ for 6 h, after which another portion of AlCl$_3$ (1.0 g, 7.40 mmol) was added to the mixture, and stirring was continued for another 5 h. The contents of the flask were cooled to ambient temperature, quenched carefully with ice-cold water. Saturated NaHCO$_3$ was added, and the aqueous phase extracted with 5% MeOH/chloroform. The resultant organic phase was washed with brine, dried (Na$_2$SO$_4$), and evaporated to isolate the crude product [5]. This crude material was triturated with a 1:1 mixture of ether/hexanes to isolate the pure compound [5] (5.80 g, 58%).

Compound [5] (2.0 g, 6.0 mmol) was dissolved in a mixture of MeOH (70 mL) and 6 N HCl (10 mL), and Pd—C (10 wt %, 0.57 g) was added. Hydrogen gas was bubbled through the stirring mixture until the reaction was complete (as monitored by MS). Then the reaction mixture was filtered through a pad of Celite to remove the palladium catalyst. The filtrate was evaporated to remove methanol, and the acidic aqueous mixture was added to sat. NaHCO$_3$ to quench, and subsequently extracted with 10% MeOH/chloroform. The organic phase was washed with brine, dried (Na$_2$SO$_4$), and evaporated to isolate the desired product [6] (1.80 g, 89%).

Compound [6] (1.80 g, 5.32 mmol) was dissolved in anhydrous CH$_2$Cl$_2$ (30 mL) at 0° C. under N$_2$. DIPEA (1.38 g, 10.64 mmol) was added to the stirring solution, followed by dropwise addition of methanesulfonyl chloride (0.67 g, 5.85 mmol). The reaction mixture was stirred at o 0° C. for 40 min, after which the solvent was removed to obtain the crude mesylate intermediate. The mesylate intermediate was dissolved in anhydrous MeOH (50 mL), and compound [7] (1.76 g, 7.95 mmol) was added to this solution followed by DIPEA (1.80 g, 5.32 mmol). This mixture was heated at reflux for 1.5 h, and then the methanol solvent was removed under reduced pressure, and the residue dissolved in chloroform. The chloroform organic phase was washed with water, brine, dried ($Na_2SO_4$), and evaporated to isolate the crude product [8], which was purified by flash chromatography using 2-5% $MeOH/CHCl_3$ as eluent to isolate the pure product [8] (2.02 g, 70%).

The ester [8] (2.0 g, 3.70 mmol) was dissolved in a mixture of MeOH/THF (1:3, 24 mL) at o 0° C., and a solution of $LiOH·H_2O$ (0.46 g, 11.10 mmol) in water (6 mL) was added. The mixture was allowed to warm to ambient temperature and stirred for 2 h. The reaction solution was diluted with EtOAc, and washed with 0.1 N HCl. The organic phase was removed and set aside, and the remaining aqueous phase was extracted with 10% $MeOH/CHCl_3$. The extract was combined with the set-aside organic phase, and combined organic phase was washed with brine, dried ($Na_2SO_4$), and evaporated to provide compound [9] (1.91 g, 99%) as a white foam.

Example 2

Preparation of Risperidone (9-yloxypetancarbamoyl)-methyl-benzoic Acid Derivative [14] (Scheme 2)

Compound [9] (700 mg, 1.33 mmol), compound [12] (440 mg, 1.46 mmol), and DIPEA (0.86 g, 1.2 mL, 6.65 mmol) were dissolved in DMF (10 mL) at 0° C. HATU (1.21 g, 3.19 mmol) was added, after which the reaction mixture was allowed to warm to ambient temperature, and stirred overnight. The following day, the reaction mixture was diluted with EtOAc, and the resulting organic phase was washed with 1 M HCl, sat. $NaHCO_3$, water and dried ($Na_2SO_4$). Removal of the solvent provided the crude product [13], which was purified by flash chromatography with 2-8% $MeOH/CHCl_3$ to obtain the pure product [13] (0.52 g, 55%) as a white solid.

Compound [13] (0.50 g, 0.7 mmol) was dissolved in anhydrous $CH_2Cl_2$ (10 mL) at 0° C. under $N_2$ and TFA (10 mL) was added to the stirring solution. The stirring was continued at o 0° C. for 3 h and at then ambient temperature for an additional 20 h. After this time, the solvent was removed under reduced pressure, and the resulting residue was suspended in water and lyophilized to dryness to yield the crude acid [14]. This dried material was dissolved with 2% $MeOH/CHCl_3$ (5 mL), and added to 200 mL of ether, causing the acid [14] to precipitate from solution. The precipitated solid was filtered, washed with ether and dried at 40° C. to obtain the desired compound [14] (0.38 g, 72%) as an off-white powder.

Example 3

General Method for Preparing s-NHS Activated Drug Derivatives from the Corresponding Acids [9] & [14]

Risperidone acid derivatives [9] & [14] were activated with EDC and s-NHS to produce the s-NHS activated esters of risperidone [10] & [15] for eventual conjugation to proteins (examples 4 and 5).

Example 3a

Preparation of s-NHS Activated Ester Risperidone (9-yloxy)pentanoic Acid Derivative [10]

Risperidone derivative [9], example 1, scheme 1, (56.8 mg) was dissolved in 5.68 mL of DMSO to which was added s-NHS (66.56 mg) and EDC (58.58 mg). The reaction mixture was stirred for 20 hours at ambient temperature under a nitrogen atmosphere to produce the s-NHS activated ester of risperidone [10]. The reaction mixture was used directly in examples 4 and 5a.

Example 3b

Preparation of s-NHS Activated Ester Risperidone (9-yloxypetancarbamoyl)-methyl-benzoic Acid Derivative [15]

Risperidone derivative [14], example 2, scheme 2 (25.0 mg) was dissolved in 2.5 mL of DMSO to which was added s-NHS (19.9 mg) and EDC (17.6 mg). The reaction mixture was stirred for 20 hours at ambient temperature under a nitrogen atmosphere to produce the s-NHS activated ester of risperidone [15]. The reaction mixtue was used directly in example 5b.

Example 4

Preparation of KLH Immunogen with Activated Hapten [10]

A protein solution of KLH was prepared by dissolving 300 mg of KLH in 20 mL of phosphate buffer (50 mM, pH 7.5), followed by addition of 4.85 mL of s-NHS activated risperidone derivative [10] prepared in Example 3a. The reaction mixture of KLH and activated risperidone derivative [10] was allowed to stir for 20 hours at room temperature to produce the risperidone [9]-KLH conjugate. The risperidone [9]-KLH conjugate was then purified by dialysis against 30% DMSO in phosphate buffer (50 mM, pH 7.5) at room temperature. Thereafter the DMSO proportion was reduced stepwise: 20%, 10% and 0%. The last dialysis was performed against phosphate buffer at 4° C. The risperidone [9]-KLH conjugate was characterized by ultraviolet-visible spectroscopy. The conjugate was diluted to a final concentration of 2 mg/mL in phosphate buffer (50 mM, pH 7.5).

Example 5a

Preparation of BSA Conjugate with Activated Hapten [10]

A protein solution of BSA was prepared by dissolving 1 g BSA in phosphate buffer (50 mM, pH 7.5) for a final concentration of 50 mg/mL. To this protein solution was added 0.83 mL of s-NHS activated risperidone derivative [10] prepared in Example 3a. The amount of s-NHS activated risperidone derivative [10] added to the protein solution of BSA was calculated for a 1:1 molar ratio between the derivative of risperidone [10] and BSA. The mixture of BSA and activated risperidone derivative [10] was allowed to stir for 18 hours at room temperature to produce the conjugate of the activated risperidone ester [10] and BSA. This conjugate was then purified by dialysis against 20% DMSO in phosphate buffer (50 mM, pH 7.5) at room temperature. Thereafter the DMSO proportion was reduced stepwise: 10% and 0%. The last dialysis was performed against phosphate buffer at 4° C. The purified risperidone [9]-BSA conjugate was characterized by UV/VIS spectroscopy.

Example 5b

Preparation of BSA Conjugate with Activated Hapten [15]

A protein solution of BSA was prepared by dissolving 1 g BSA in phosphate buffer (50 mM, pH 7.5) for a final concentration of 50 mg/mL. To 10.0 mL of the protein solution of BSA while stirring on ice, was added 0.620 mL of s-NHS activated risperidone derivative [15] prepared in Example 3b. The amount of s-NHS activated risperidone derivative [15] added to the protein solution of BSA was calculated for a 1:1 molar ratio between the derivative of risperidone [15] and BSA. The mixture of BSA and activated risperidone derivative [15] was allowed to stir for 18 hours at room temperature to produce the conjugate of the activated risperidone ester [15] and BSA. This conjugate was then purified by dialysis against 15% DMSO in phosphate buffer (50 mM, pH 7.5) at room temperature. Thereafter the DMSO proportion was reduced stepwise: 10%, 5%, and 0%. The last dialysis was performed against phosphate buffer at 4° C. The purified risperidone [14]-BSA conjugate was characterized by UV/VIS spectroscopy.

Example 6a

Preparation of Polyclonal Antibodies to Risperidone [9]

Ten female BALB/c mice were immunized i.p. with 100 μg/mouse of risperidone [9]-KLH immunogen, as prepared in Example 4, emulsified in Complete Freund's Adjuvant. The mice were boosted once, four weeks after the initial injection with 100 μg/mouse of the same immunogen emulsified in Incomplete Freund's Adjuvant. Twenty days after the boost, test bleeds containing polyclonal antibodies from each mouse were obtained by orbital bleed. The test bleeds were fractionated by centrifugation to yield anti-sera. The anti-sera from these test bleeds, which contain polyclonal antibodies to risperidone [9]-KLH immunogen, were evaluated in Examples 8a and 9.

Example 6b

Preparation of Monoclonal Antibodies to Risperidone [9]

Mice from example 6a that were immunized with risperidone [9]-KLH prepared in 4 were used to produce monoclonal antibodies. For monoclonal antibodies starting three days before the fusion, the mice were injected i.p. with 400 μg (3 days before fusion), 200 μg (2 days before fusion), and 200 μg (1 day before fusion) of risperidone [9]-KLH in PBS/DMSO prepared in example 4. Spleen cells were isolated from the selected mice and fused with $2 \times 10^7$ SP2/0 cells with 50% polyethylene glycol 1500 according to the method of Coligan, J. E. et al., eds., *Current Protocols in Immunology*, 2.5.1-2.5.8, (1992), Wiley & Sons, NY. The fused cells were plated on ten 96-well plates in DMEM/F12 supplemented with 20% FetalClone I, 2% L-glutamine (100 mM) and 2% 50×HAT. Two to three weeks later, the hybridoma supernatant was assayed for the presence of anti-risperidone antibodies by ELISA (as in example 8b). Cells from the wells that gave positive ELISA results (example 8b) were expanded to 24 well plates. Clones positive by ELISA were subcloned twice by limiting dilution according to the method disclosed in Coligan, J. E. et al., eds., *Current Protocols in Immunology*, 2.5.8 2.5.17, 1992, Wiley & Sons, NY. Hybridoma culture supernatants containing monoclonal antibody from selected subclones were confirmed for risperidone binding by a competitive ELISA (example 9). These monoclonal antibodies were tested for risperidone binding and cross-reactivity to a major risperidone metabolite, 7-hydroxy-risperidone, by indirect competitive microtiter plate assay as described in example 9.

Example 7a

Microtiter Plate Sensitization Procedure with Risperidone [9]-BSA Conjugate

The ELISA method for measuring risperidone concentrations was performed in polystyrene microtiter plates (Nunc MaxiSorp F8 Immunomodules) optimized for protein binding and containing 96 wells per plate. Each well was coated with risperidone [9]-BSA conjugate (prepared as in Example 5a) by adding 300 μL of risperidone [9]-BSA conjugate at 10 mg/mL in 0.05M sodium carbonate, pH 9.6, and incubating for three hours at room temperature. The wells were washed with 0.05M sodium carbonate, pH 9.6 and then were blocked with 375 μL of 5% sucrose, 0.2% sodium caseinate solution for 30 minutes at room temperature. After removal of the post-coat solution the plates were dried at 37° C. overnight.

Example 7b

Microtiter Plate Sensitization Procedure with Risperidone [14]-BSA Conjugate

The ELISA method for measuring risperidone concentrations was performed in polystyrene microtiter plates (Nunc MaxiSorp F8 Immunomodules) optimized for protein binding and containing 96 wells per plate. Each well was coated with risperidone [14]-BSA conjugate (prepared as in Example 5b) by adding 300 μL of risperidone [14]-BSA conjugate at 10 μg/mL in 0.05M sodium carbonate, pH 9.6, and incubating for three hours at room temperature. The wells were washed with 0.05M sodium carbonate, pH 9.6 and then were blocked with 375 μL of 5% sucrose, 0.2% sodium caseinate solution for 30 minutes at room temperature. After removal of the post-coat solution the plates were dried at 37° C. overnight.

Example 8a

Antibody Screening Procedure—Titer

This procedure is to find the dilution of antibody or antiserum to be tested for displacement as in Example 9. The ELISA method for screening risperidone antibodies (produced in Example 6) was performed with the microtiter plates that were sensitized with risperidone-BSA conjugate prepared in Examples 7a and 7b. The antibody screening assay was performed by diluting the murine serum from test bleeds (as in Example 6) containing polyclonal risperidone antibodies to 1:2,000, 1:6,000, 1:15,000 and 1:54,000 (volume/volume) in phosphate buffered saline containing 0.1% BSA and 0.01% thimerosal. For evaluation of monoclonal antibodies, hybridoma supernatants of Example 6b, which were found to be positive for the presence of antibody by the procedure of Example 8b were diluted 1:2, 1:4, 1:16, etc. (volume/volume) in phosphate buffered saline containing 0.1% BSA and 0.01% thimerosal. To each well of risperidone-BSA sensitized wells (prepared in Examples 7a and 7b) 50 μL phosphate buffered saline containing 0.1% BSA and 0.01% thimerosal and 50 μL of diluted antibody were added and incubated for 10 minutes at room temperature with shaking. During this incubation antibody binds to the risperidone-BSA conjugate passively absorbed in the wells (Examples 7a and 7b). The wells of the plates were washed three times with 0.02 M TRIS, 0.9% NaCl, 0.5% Tween-80 and 0.001% thimerosal, pH 7.8 to remove any unbound antibody. To detect the amount of risperidone antibody bound to the risperidone-BSA conjugate in the wells, 100 μL of a goat anti-mouse antibody-HRP enzyme conjugate (Jackson Immunoresearch) diluted to a specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody-HRP enzyme conjugate binds to risperidone antibodies in the wells, the plates were again washed three times to remove unbound goat anti-mouse antibody-HRP enzyme conjugate. To develop a measurable color in the wells washing was followed by the addition of 100 μL of TMB (TMB Substrate, BioFx), the substrate for HRP, to develop color during a 10 minute incubation with shaking at room temperature. Following the incubation for color development, 50 μL of stop solution (1.5% sodium fluoride in di $H_2O$) was added to each well to stop the color development and after 20 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing antibody dilution of the antibody measured (x-axis) vs. absorbance 650 nm (y-axis) and interpolating the titer at an absorbance of 1.5. The titer which produced absorbance of 1.5 determined the concentration (dilution) of antibody used in the indirect competitive microtiter plate assay described in Example 9.

Example 8b

Antibody Screening Procedure—Monoclonal Screening

The ELISA method for screening risperidone monoclonal antibodies (produced in example 6b) was performed with the microtiter plates that were sensitized with risperidone-BSA as described in example 7a. To each well of risperidone-BSA sensitized wells (prepared in example 7) 50 μL phosphate buffered saline containing 0.1% BSA and 0.01% thimerosal and then 50 μL of monoclonal culture supernatant were added and incubated for 10 minutes at room temperature with shaking. During this incubation antibody binds to the risperidone-conjugate in the well. The wells of the plates were washed three times with 0.02 M TRIS, 0.9% NaCl, 0.5% Tween-80 and 0.001% thimerosal, pH7.8 to remove any unbound antibody. To detect the amount of risperidone antibody bound to the risperidone-BSA conjugate in the wells, 100 μL of a goat anti-mouse antibody-HRP enzyme conjugate (Jackson Immunoresearch) diluted 1/3000 in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody-HRP enzyme conjugate binds to risperidone antibodies in the wells, the plates were again washed three times to remove unbound goat anti-mouse antibody-HRP enzyme conjugate. To develop a measurable color in the wells washing was followed by the addition of 100 μL of TMB (TMB Substrate, BioFx), the substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured. Samples with an absorbance of greater than three or more times background were designated as positive. Fifty samples with highest absorbance were expanded to 24 well plates, as described in Example 6b.

Example 9

Indirect Competitive Microtiter Plate Immunoassay Procedure Determining $IC_{50}$ and Cross-Reactivity for Antibodies to Risperidone The ELISA method for determining $IC_{50}$ values and cross-reactivity was performed with the microtiter plates that were sensitized with risperidone-BSA conjugates as described in Examples 7a and 7b. The analytes-risperidone and paliperidone, and their inactive metabolites 7-hydroxy-risperidone and N-dealkyl-risperidone—were diluted in $diH_2O$ over a concentration range of 1 to 10,000 ng/mL when using risperidone [9]-BSA microtiter plates (as in Example 7a) or 0.5 to 1,000 ng/mL when using risperidone [14]-BSA microtiter plates (as in Example 7b). Each of the assays were performed by incubating 50 μL of the analyte solution with 50 μL of one of the anti-sera selected from the polyclonal antibodies produced in Example 6a with the immunogen of Example 4 or 50 μL of one of the selected monoclonal antibodies produced in Example 6b. The assays were all performed by diluting the concentration of the anti-sera or monoclonal antibodies in each of the wells to the titer determined in Example 8a. During the 10 minute incubation (at room temperature with shaking) there is a competition of antibody binding for the risperidone-BSA conjugate in the well (produced in Examples 7a and 7b) and the analyte in solution. Following this incubation the wells of the plate were washed three times with 0.02 M TRIS, 0.9% NaCl, 0.5% Tween-80 and 0.001% thimerosal, pH 7.8 to remove any material that was not bound. To detect the amount of risperidone antibody bound to the risperidone-BSA conjugate in the wells (produced in Examples 7a and 7b), 100 μL of a goat anti-mouse antibody-HRP enzyme conjugate (Jackson Immunoresearch) diluted to a predetermined specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody-HRP enzyme conjugate binds to risperidone antibodies in the wells, the plates were again washed three times to remove unbound secondary conjugate. To develop a measurable color in the wells washing was followed by the addition of 100 μL of TMB (TMB Substrate, BioFx), the substrate for HRP, to develop color in a 10 minute incubation with shaking at room temperature. Following the incubation for color development, 50 μL of stop solution (1.5% sodium fluoride in di $H_2O$) was added to each well to stop the color development and after 20 seconds of shaking the absorbance was determined at 650 nm (Molecular Devices Plate Reader). The amount of antibody in a well was proportional to the absorbance measured and inversely proportional to the amount of risperidone in the sample. The $IC_{50}$'s of risperidone and paliperidone were determined by constructing dose-response curves with the absorbance in the wells plotted versus analyte concentration in the wells. The absorbance of the color in the wells containing analyte was compared to that with no analyte and a standard curve was generated. The $IC_{50}$ value for a given analyte was defined as the concentration of analyte that was required to have 50% of the absorbance of the wells containing no analyte. The cross-reactivity was calculated as the ratio of the $IC_{50}$ for risperidone to the $IC_{50}$ for paliperidone and expressed as a percent. When measured with this pool of antibodies, the percent cross-reactivities relative to risperidone for paliperidone were 100±20%. Results for polyclonal antibodies to risperidone are in table I below. Results for monoclonal antibodies to risperidone are in table II.

TABLE I

Cross-reactivity of competitive immunoassay using polyclonal antibodies to risperidone (Example 6a).

| | Bleed # | G1M1 | G1M3 | G2M1 | G2M5 |
|---|---|---|---|---|---|
| Analyte | Risperidone | 100% | 100% | 100% | 100% |
| | Paliperidone | 81% | 80% | 98% | 81% |
| | 7-hydroxy-risperidone | 50% | 66% | 65% | 69% |
| | N-dealkyl-risperidone | 0.02% | 0.07% | 0.09% | 0.1% |

TABLE II

Cross-reactivity of competitive immunoassay using monoclonal antibodies to risperidone (Example 6b).

| | Monoclonal antibody number | |
|---|---|---|
| Analyte | 4B9-21 | 5D5-3 |
| Risperidone | 100% | 100% |
| 7-hydroxy-risperidone | 30% | 39% |

As seen from these tables, the antibodies of this invention are substantially selectively reactive with the active form of risperidone as well as substantially cross-reactive with the active metabolite paliperidone, and have low cross-reactivity with the inactive metabolites 7-hydroxy-risperidone and N-dealkyl-risperidone.

What is claimed:

1. An immunoassay for detecting active pharmaceutically anti-psychotic drugs selected from the group consisting of risperidone, paliperidone and mixtures thereof comprising providing a mixture containing a sample, a conjugate of a carrier with a ligand having the formula:

III

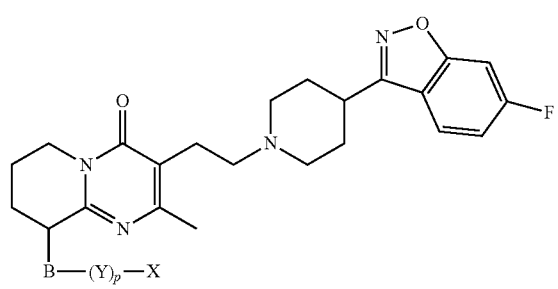

wherein B is $$-O-CH_2-, \quad -O-\underset{\underset{O}{\|}}{C}-CH_2-,$$

$$-\underset{\underset{O}{\|}}{C}-O-CH_2-, \quad -\underset{\underset{O}{\|}}{C}-NH-CH_2-,$$

$$-HN-\underset{\underset{O}{\|}}{C}-CH_2-, \quad -HN-\underset{\underset{O}{\|}}{C}-NH-, \text{ or}$$

$$-HN-\underset{\underset{S}{\|}}{C}-NH-$$

Y is an organic spacing group;

X is a terminal functional group capable of binding to a carrier; and p is an integer from 0 to 1;

and an antibody selectively reactive with said pharmaceutically active anti-psychotic drugs having little substantial reactivity with the pharmacologically inactive risperidone and paliperidone metabolite, 7-hydroxy-risperidone and having no substantial cross-reactivity with other pharmacologically inactive risperidone and paliperidone metabolites, said reactivity of said antibody with 7 hydroxy-risperidone being less than 40% and said cross reactivity of said antibody with the other pharmaceutically inactive metabolites being less than 5%, said reactivity and cross reactivity being based upon said antibody's combined reactivity with both risperidone and paliperidone, and causing the pharmaceutically active anti-psychotic drug and said conjugate in said sample to bind with said antibody and thereafter measuring the amount of said conjugate in said sample that is bond or unbound to said antibody whereby the presence of the anti-psychotic drugs in said sample can be detected.

2. The immunoassay of claim 1 wherein the sample is a human sample.

3. The immunoassay of claim 2 wherein the presence of said pharmaceutically active anti-psychotic drug is quantified by measuring the amount of conjugate which is bound or unbound to said antibody.

4. The immunoassay of claim 3 wherein the pharmaceutically active anti-psychotic drugs are the selected from the group consisting of risperidone and paliperidone.

5. The immunoassay of claim 4 wherein said human sample is a sample taken from a patient treated with risperidone and said immunoassay measures the amount of risperidone and paliperidone in the sample.

6. The immunoassay of claim 5 wherein said human sample is as sample take from a patient treated with paliperidone and the immunoassay measures the amount of paliperidone in said sample.

7. The immunoassay of claim 1 wherein said antibody is generated from an immunogen comprising an immunogenic carrier containing polyamine polymer conjugated with a ligand of the formula:

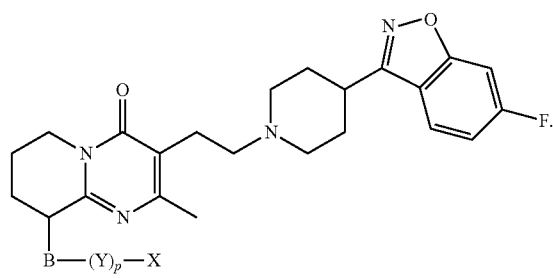

8. The immunoassay of claim 3, wherein the antibody is attached to a solid support.

9. The immunoassay of claim 8, wherein the solid support is microtitor plates.

10. The immunoassay of claim 8, wherein the solid support is nanoparticles.

11. The immunoassay of claim 7, wherein said antibody is derived from mice, rabbits, sheep or rats.

12. The immunoassay of claim 11, wherein said antibody is a monoclonal antibody.

13. A kit for determining the presence of pharmaceutical active anti-psychotic drugs selected from the group consisting of risperidone and paliperidone in a patient sample comprising separate reagents packaged in separate containers, one of said reagents being a conjugate of a carrier with a ligand of the formula:

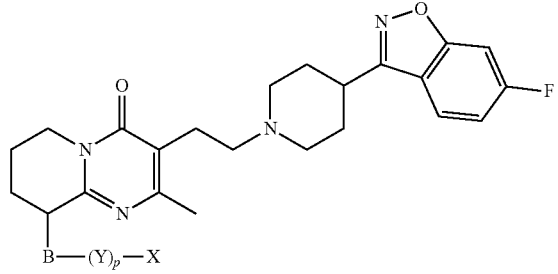

wherein B is

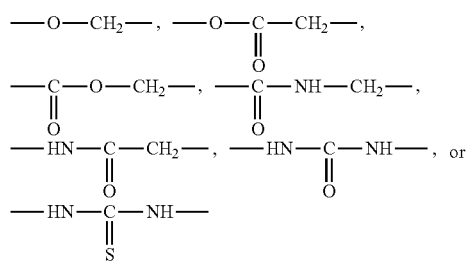

Y is an organic spacing group;
X is a terminal functional group capable of binding to a carrier; and
p is an integer from 0 to 1;

and the other reagent being an antibody which is selectively reactive with a pharmaceutically active anti-psychotic drug selected from the group of consisting of risperidone and paliperidone wherein said antibody reacts with risperidone and paliperidone and has little substantial reactivity with the pharmacologically inactive risperidone and paliperidone metabolite, 7-hydroxy-risperidone, and does not substantial cross-reactivity with other pharmacologically inactive risperidone and paliperidone metabolites, said reactivity of said antibody with 7 hydroxy-risperidone being less than 40% and said cross reactivity of said antibody with the other pharmaceutically inactive metabolites being less than 5%, said reactivity and cross reactivity being based upon said antibody's combined reactivity with both risperidone and paliperidone.

14. The kit of claim 13 wherein p is 1.

15. The kit of claim 14 wherein B is —O—CH$_2$—.

16. The kit of claim 15 where Y is lower alkylene.

17. The kit of claim 16 where X is

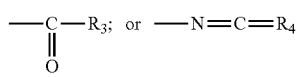

wherein $R_3$ is hydrogen, a halide, a hydroxyl, or taken together with its attached oxygen atom forms a reactive ester and $R_4$ is oxygen or sulfur.

18. The kit of claim 17, wherein X is

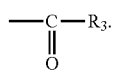

19. The kit of claim 13 wherein Y is

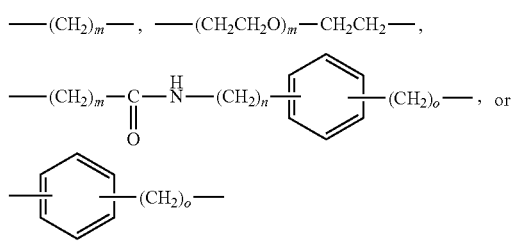

wherein n and o are integers from 0 to 6, and m is an integer from 1 to 6.

20. The kit of claim 19, wherein Y is

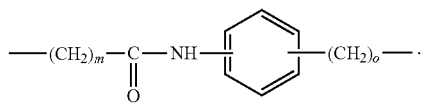

* * * * *